United States Patent [19]
Salzman et al.

[11] Patent Number: 5,856,360
[45] Date of Patent: Jan. 5, 1999

[54] PHARMACEUTICAL METHOD FOR THE TREATMENT OF SEVERE BLOOD LOSS AND FOR THE INHIBITION OR TREATMENT OF HEMORRHAGIC SHOCK

[75] Inventors: Andrew L. Salzman; Csaba Szabó, both of Cincinnati, Ohio

[73] Assignee: Children's Hospital Medical Center, Cincinnati, Ohio

[21] Appl. No.: 642,468

[22] Filed: May 3, 1996

[51] Int. Cl.$^6$ .......................... A61K 31/175; A61K 31/55
[52] U.S. Cl. .......................... 514/593; 514/212; 514/921
[58] Field of Search ................................. 514/593, 212, 514/921

[56] References Cited

FOREIGN PATENT DOCUMENTS 630888A  12/1994  European Pat. Off. .

OTHER PUBLICATIONS

DiPiro et al., "Pharmacotherapy, A Pathophysiologic Approach" Elsevier Science, New York, NY (1989) pp. 1542–1543.

Sewster et al., "Facts and Comparisons", J. B. Lipincott Co., St. Louis, Mo., (Jun. 1985), p. 52.

"The ATP–Sensitive K$^+$ Channel Mediates Hypotension in Endotoxemia and Hypoxic Lactic Acidosis in Dog", by: Donald W. Landry and Juan A. Oliver, (J. Clin. Invest., vol. 89, Jun., 1992), pp. 2071–2074.

T. Norske Laegeforen, vol. 95, No. 32, 1975, Norway, pp. 1825–1830, Dedichen, H., "Blodningssjokk".

Lakartidningen, vol. 78, No. 38, 1981, Sweden, pp. 3275–3278, Haljamae et al., "Cellulara Aspekter Pa Patofysiologi Och Terapi Vid Hypovolemisk Chock".

Science, vol. 270, No. 5239, 17 Nov. 1995, pp. 1166–1170, Inagaki, N. et al., "Reconstitution of /Katp: An Inward Rectifier Subunit Plus The Sulfonylurea Receptor".

ENDOCRINOLOGY, vol. 88, No. 1, Jan. 1971, pp. 138–143, Cerchio et al., "Serum Insulin and Growth Hormone Response to Hemorrhagic Shock".

Eur J Pharmacol, May 30, 1991, 198 (1) P101–4, Netherlands, Muller, M. et al.: "Chlorpromazine and related phenothiazines inhibit the ATP—sensitive K+channel".

Primary Examiner—Marianne M. Cintins
Assistant Examiner—M. Moezie
Attorney, Agent, or Firm—Wood, Herron & Evans, L.L.P.

[57] ABSTRACT

This invention is directed to a pharmacologically acceptable composition for inhibiting or treating hemorrhagic shock in a mammal. The composition includes a $K_{ATP}$ inhibitor and a pharmacologically acceptable carrier, with the $K_{ATP}$ inhibitor being present in an amount sufficient to inhibit or treat hemorrhagic shock in the mammal. The invention is also directed to a method for inhibiting or treating hemorrhagic shock in a mammal. The method includes administering to the mammal an amount of a $K_{ATP}$ channel inhibitor sufficient to inhibit or treat hemorrhagic shock in the mammal. In a preferred form of the invention, the $K_{ATP}$ channel inhibitor is selected from the group consisting of a sulfonylurea, a guanidine, a phenothiazine, an imidazoline, TMB-8 (also known as (8-N, N-diethylamino) octyl-3,4,5-trimethoxybenzoate), 2,3-butanedione monoxime, disopyramide, gliquidone, chlorpromazine, AMP-NPP (also known as 5'-adenylylamidodiphosphate), flecainide, MS-551 (also known as 1,3-dimethyl-6-(2-[N-(2-hydroxyethyl)-3-(4-nitrophenyl) propylamino]ethylamino)-2,4(1H,3H)-pyrimidinedione HCl) and combinations thereof.

14 Claims, 6 Drawing Sheets

PHARMACEUTICAL METHOD FOR THE TREATMENT OF SEVERE BLOOD LOSS AND FOR THE INHIBITION OR TREATMENT OF HEMORRHAGIC SHOCK

BACKGROUND OF THE INVENTION

This invention relates to the treatment of a mammal with severe blood loss or hemorrhagic shock and, more particularly to a pharmaceutical composition and method for the treatment of severe blood loss, and for the inhibition or treatment of hemorrhagic shock in a mammal.

Hemorrhagic shock is a life-threatening condition brought on by severe blood loss. For example, hemorrhagic shock may originate from internal or external hemorrhage, gun shot wounds, severe trauma or any other condition associated with blood loss. Unfortunately, because of the severity and complexity of hemorrhagic shock, a patient is likely to die unless treated during a relatively short treatment window, generally known as the "golden hour".

Hemorrhagic shock is an extremely complex process, stimulating multiple injury pathways. That is, the pathophysiology of hemorrhagic shock is multifactorial. For example, hemorrhagic shock stimulates the release of cytokines and nitric oxide, as well as the formation of peroxynitrite and the generation of superoxide radical. In addition, hemorrhagic shock stimulates pathways which release platelet activating factor, and induces alterations in the complement cascade and coagulation cascade. Furthermore, hemorrhagic shock stimulates neuroendocrine responses, electrolyte disturbances and metabolic changes. Accordingly, the treatment and management of a patient experiencing hemorrhagic shock is extremely complex.

The initial phase of hemorrhagic shock, unless rapidly corrected, is followed by progressive tissue ischemia, end-organ disfunction and refractory vascular failure. Hemorrhagic shock also is associated with early vasomotor paralysis and cardiovascular collapse. Accordingly, conventional resuscitation methods have been directed toward hemostasis and intravenous infusion of sufficiently large volumes of fluid, preferably blood, in order to restore cardiac index, improve oxygen-carrying capacity and minimize cellular hypoxia. Although this approach may be well suited for the in-patient setting, it is impractical in field situations where the supply of resuscitation fluid is limited. Therefore, it would be extremely beneficial to have a method for treating hemorrhagic shock which does not require large volumes of resuscitation fluid.

In addition, traditional resuscitation methods using pharmaceutical intervention usually involve a catecholamine, such as norepinephrine for example, which rapidly loses its effectiveness within one hour, and thus is of limited clinical utility. Accordingly, it would be extremely desirable to have a method and composition for treating hemorrhagic shock which does not lose its effectiveness in a short period of time.

SUMMARY OF THE INVENTION

This invention is directed to a pharmacologically acceptable composition for inhibiting or treating hemorrhagic shock in a mammal. The composition includes a $K_{ATP}$ inhibitor and a pharmacologically acceptable carrier, with the $K_{ATP}$ inhibitor being present in an amount sufficient to inhibit or treat hemorrhagic shock in the mammal.

The invention also is directed to a method for inhibiting or treating hemorrhagic shock in a mammal. The method includes administering to the mammal an amount of a $K_{ATP}$ channel inhibitor sufficient to inhibit or treat hemorrhagic shock in the mammal.

In a preferred form of the invention, the $K_{ATP}$ channel inhibitor is selected from the group consisting of a sulfonylurea, a guanidine, a phenothiazine, an imidazoline, TMB-8 (also known as (8-N, N-diethylamino) octyl-3, 4, 5-trimethoxybenzoate), 2, 3-butanedione monoxime, disopyramide, gliquidone, chlorpromazine, AMP-NPP, flecainide, MS-551 (also known as 1,3-dimethyl-6-(2-[N-(2-hydroxyethyl)-3-(4-nitrophenyl)propylamino] ethylamino)-2,4(1H,3H)-pyrimidinedione HCl)and combinations thereof.

In another preferred form of the invention, the $K_{ATP}$ channel inhibitor is a sulfonylurea compound. When a sulfonylurea compound is used, the sulfonylurea may preferably be glibenclamide, tolazamide, acetohexamide, tolbutamide or a combination thereof.

Preferably, the composition of the present invention is formulated for parenteral administration and the method involves administering the $K_{ATP}$ channel inhibitor parenterally. If a carrier, such as a solvent, is used, the carrier may suitably be Ringers-Lactate, a sodium chloride solution, red blood cells, whole blood, plasma, a crystalloid solution, a colloid solution, dextrose, albumin, ethanol, sodium hydroxide, dimethylsulfoxide, water, or the like, and combinations thereof. In a preferred form of the invention, the carrier is Ringers-Lactate with 10% (weight/volume) dextrose. Additionally, when the $K_{ATP}$ channel inhibitor is in combination with a carrier, the inhibitor preferably represents from about 0.01% (weight/volume) to about 10% (weight/volume) of the composition.

The potassium ATP channel inhibitor may advantageously be combined with any of a number of other ingredients. Examples of such ingredients include an anti-oxidant, a sedative, an anesthetic, a catecholamine, an antibiotic, a glucocorticoid, a histamine receptor blocker, calcium, a bacteriostat, an inhibitor of a free-radical-producing enzyme, a non-steroidal anti-inflammatory agent, a suspending agent, a stabilizing agent, a color, a dye, a preservative or combinations thereof.

With respect to dosing, the $K_{ATP}$ channel inhibitor may suitably be administered at a dose of from about 5 mg per day to about 17.5 g per day. In a preferred form of the invention, the inhibitor is administered at a dose of from about 5 mg per day to about 10 g per day, and in a more preferred form, the inhibitor is administered at a dose of from about 200 mg per day to about 5 g per day.

Under conditions of severe blood loss, the composition and method are particularly beneficial in improving systemic and regional hemodynamics, and in improving tissue metabolism.

The method of the present invention may be performed by administering the $K_{ATP}$ channel inhibitor with or without a large volume of resuscitation fluid. If a large volume of resuscitation fluid is not used, the inhibitor generally is administered with a small amount of a solvent in order to deliver the inhibitor. Alternatively, when a large volume of resuscitation fluid is administered as a part of the method, the resuscitation fluid may suitably be Ringers-Lactate, a sodium chloride solution, red blood cells, whole blood, plasma, a crystalloid solution, a colloid solution, dextrose, albumin, ethanol, sodium hydroxide, dimethylsulfoxide, water or combinations thereof.

The composition and method offer several benefits and advantages in inhibiting or treating hemorrhagic shock. For example, the $K_{ATP}$ channel inhibitors have been shown to have a dramatically beneficial impact on systemic and regional hemodynamics, tissue metabolism and, importantly, survival in mammals experiencing hemorrhagic shock, without the use of traditional large volumes of resuscitation fluid. Therefore, although the composition and method may be used in inhibiting or treating hemorrhagic shock in any setting, the invention is particularly advantageous in the field setting, where it may be difficult to transport and maintain large volumes of resuscitation fluid. In addition, the $K_{ATP}$ channel inhibitors of the present invention maintain their vasopressor effectiveness over a longer period of time than traditional pharmaceutical therapies such as norepinephrine, which tends to lose its effectiveness over a relatively brief period.

DETAILED DESCRIPTION OF THE INVENTION

This invention is directed to a pharmacologically acceptable composition for inhibiting or treating hemorrhagic shock in a mammal. The composition includes a $K_{ATP}$ inhibitor and a pharmacologically acceptable carrier, with the $K_{ATP}$ inhibitor being present in an amount sufficient to inhibit or treat hemorrhagic shock in the mammal.

The invention also is directed to a method for inhibiting or treating hemorrhagic shock in a mammal. The method includes administering to the mammal an amount of a $K_{ATP}$ channel inhibitor sufficient to inhibit or treat hemorrhagic shock in the mammal.

In a preferred form of the invention, the $K_{ATP}$ channel inhibitor is selected from the group consisting of a sulfonylurea, a guanidine, a phenothiazine, an imidazoline, TMB-8 (also known as (8-N, N-diethylamino) octyl-3, 4, 5-trimethoxybenzoate), 2, 3-butanedione monoxime, disopyramide, gliquidone, chlorpromazine, AMP-NPP (also known as 5'-adenylylimidodiphosphate), flecainide, MS-551 ([1 ,3-dimethyl-6-(2-[N-(2-hydroxyethyl)-3-(4-nitrophenyl) propylamino] ethylamino)-2,4(1 H,3H)-pyrimidinedione HCl) and combinations thereof.

In another preferred form of the invention, the $K_{ATP}$ channel inhibitor is a sulfonylurea compound. When a sulfonylurea compound is used, the sulfonylurea may preferably be glibenclamide, tolazamide, acetohexamide, tolbutamide or a combination thereof.

Pharmaceutical formulations of the $K_{ATP}$ channel inhibitor may include those suitable for intravenous administration. The formulations may, where appropriate, be conveniently presented in discrete dosage units and may be prepared by any of the methods well known in the art of pharmacy. All such pharmacy methods include the steps of bringing into association the active compound with liquid carriers or finely divided solid carriers or both as needed and then, if necessary, shaping the product into the desired formulation.

Formulations for parenteral administration include: aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline, water-for-injection, immediately prior to use. Alternatively, the formulations may be presented for continuous infusion. Extemporaneous injection solutions and suspensions may be prepared from sterile powders, granules and tablets of the kind previously described.

Preferably, the composition of the present invention is formulated for parenteral administration and the method involves administering the $K_{ATP}$ channel inhibitor parenterally. If a carrier, such as a solvent, is used, the carrier may suitably be Ringers-Lactate, a sodium chloride solution, red blood cells, whole blood, plasma (e.g., the fresh-frozen plasma, Hetestarch), a crystalloid solution, a colloid solution, dextrose, albumin, ethanol, sodium hydroxide, dimethylsulfoxide, water, or the like, and combinations thereof. When dextrose, albumin or sodium chloride is used, the preferred concentration is about 0–15% for dextrose, about 0–25% for albumin and about 0–3% for sodium chloride. In a preferred form of the invention, the carrier is Ringers-Lactate with 10% (weight/volume) dextrose. Additionally, when the $K_{ATP}$ channel inhibitor is in combination with a carrier, the inhibitor preferably represents from about 0.01 % (weight/volume) to about 10% (weight/volume) of the composition.

The potassium ATP channel inhibitor may advantageously be combined with any of a number of other therapeutic or nontherapeutic agents. Examples of such agents or ingredients include anticoagulants, anti-oxidants, sedatives, anesthetics, catecholamines, antibiotics, glucocorticoids, histamine receptor blockers, calcium, bacteriostats, inhibitors of free-radical-producing enzymes, non-steroidal anti-inflammatory agents, suspending agents, stabilizing agents, colors, dyes, preservatives or combinations thereof. It should be understood that in addition to the ingredients particularly mentioned above, the formulations of this invention may include other agents conventional in the art having regard to the type of formulation in question.

Preferred unit dosage formulations are those containing an effective dose, as recited below, or an appropriate fraction thereof, of the active ingredient. The $K_{ATP}$ channel inhibitor may suitably be administered at a dose of from about 0.1 mg/kg to about 250 mg/kg per day. For adult humans, the dose range is generally from about 5 mg per day to about 17.5 g per day. In a preferred form of the invention, the inhibitor is administered at a dose of from about 5 mg per day to about 10 g per day, and in a more preferred form, the inhibitor is administered at a dose of from about 200 mg per day to about 5 g per day.

The pharmaceutical composition preferably is administered by injection (intravenous or subcutaneous), and the precise amount administered to a patient will be the responsibility of the attendant physician. However, the dose employed will depend upon a number of factors, including the age and sex of the patient, the precise disorder being treated, and its severity. Also the route of administration may vary depending upon the condition and its severity.

Under conditions of severe blood loss, the composition and method are particularly beneficial in improving systemic and regional hemodynamics, and in improving tissue metabolism.

The method of the present invention may be performed by administering the $K_{ATP}$ channel inhibitor with or without a large volume of resuscitation fluid. If a large volume of resuscitation fluid is not used, the inhibitor generally is administered with a small amount of a solvent in order to deliver the inhibitor. Alternatively, when a large volume of resuscitation fluid is administered as a part of the method, the resuscitation fluid may suitably be Ringers-Lactate, a sodium chloride solution, red blood cells, whole blood, plasma, a crystalloid solution, a colloid solution, dextrose, albumin, ethanol, sodium hydroxide, dimethylsulfoxide, water or combinations thereof.

The inhibitors of the $K_{ATP}$ channels, in pure form or in a pharmaceutically and clinically acceptable solution, will find benefit in treating conditions and disorders where there is a prior history of severe blood loss. For example, the inhibitors of the $K_{ATP}$ channels may be used to treat hemorrhagic shock originating from internal or external hemorrhage, gunshot wounds, severe trauma, and other conditions associated with blood loss.

The inhibitors of the $K_{ATP}$ channels will enhance and prolong the efficacy of traditional fluid resuscitation strategies. The treatment can and should be used with all standard therapeutic regimens used in the operating room, intensive care unit, emergency room, on the battlefield, and in the civilian field setting, and all other places where treatment of hemorrhagic shock is required.

The composition and method offer several benefits and advantages in inhibiting or treating hemorrhagic shock. For example, the $K_{ATP}$ channel inhibitors have been shown to have a dramatically beneficial impact on systemic and regional hemodynamics, tissue metabolism and, importantly, survival in mammals experiencing hemorrhagic shock, without the use of traditional large volumes of resuscitation fluid. Therefore, although the composition and method may be used in inhibiting or treating hemorrhagic shock in any setting, the invention is particularly advantageous in the field setting, where it may be difficult to transport and maintain large volumes of resuscitation fluid. In addition, the $K_{ATP}$ channel inhibitors of the present invention maintain their vasopressor effectiveness over a longer period of time than traditional pharmaceutical therapies, such as norepinephrine which tends to lose its effectiveness over a relatively brief period.

The following Examples are provided by way of illustration, and are not intended to limit the scope of the invention.

EXAMPLE 1

This example (FIGS. 1A and 1B) illustrates the effect of glibenclamide and tolazamide treatment on MAP (FIG. 1 A) and survival (FIG. 1B) of anesthetized rats subjected to severe hemorrhagic shock.

Surgical Procedures

The animal experiments have been performed in accordance with National Institutes of Health guidelines and with the approval of the Animal Care and Use Committee of the Children's Hospital Research Foundation, Cincinnati, Ohio. In these experiments, Male Wistar rats weighing 280–300 g (Charles River Laboratories, Wilmington, Mass.) were anesthetized with sodium thiopentol (120 mg/kg, i.p.) (Abbott Laboratories, Chicago, Ill.) and instrumented, as described in Szabo et al., "Peroxynitrite-mediated oxidation of dihydrorhodamine 123 occurs in early stages of endotoxic and hemorrhagic shock and ischemia-reperfusion injury", *FEBS Lett*, 1995, 372:229–232. All animals were pretreated with heparin (500 U/kg i.v.). The trachea was cannulated to facilitate respiration and temperature was maintained at 37° C. using a homeothermic blanket. The right carotid artery was cannulated and connected to a pressure transducer for the measurement of phasic and mean arterial blood pressure (MAP) and heart rate, which were digitized using a Maclab A/D convertor (AD Instruments, Milford, Mass.), and stored and displayed on a Macintosh personal computer. The left femoral vein was cannulated for the administration of drugs. The right femoral artery was cannulated for blood withdrawal. Upon completion of the surgical procedure, cardiovascular parameters were allowed to stabilize for 10 min.

Hemorrhagic Shock Model

Ten minutes after the completion of the surgical procedure, rats were subjected to a severe hemorrhagic shock by withdrawing blood from the femoral artery into a reservoir until MAP stabilized at 35 mm Hg. In this model, the rate of blood withdrawal was approximately 0.3 mL/min, and the volume of blood withdrawn was approximately 25 mL/kg, and was not different between individual groups. After the end of blood withdrawal (approx. 25 min after the initiation of bleeding), vehicle or drug treatment was administered. The times represented in FIG. 1 are relative to the end of the hemorrhage. Animals were divided into 3 groups. In the control group, dimethylsulfoxide, the vehicle for glibenclamide and tolazamide was administered (n=13).

In the two treated groups, glibenclamide (Sigma, St. Louis, Mo.) (n=13) or tolazamide (Sigma) (n=9) was administered as a 10 mg/kg slow i.v. bolus in 0.3 ml saline, followed by an infusion of 10 mg/kg/h in 0.3 ml saline. Thereafter, MAP was monitored until t=60 min. In the vehicle-treated group, after the end of bleeding, no significant compensatory efforts were observed and no additional blood was withdrawn. Animals that died before the end of the experiment were excluded from the calculation of blood pressure or heart rate. Thus, MAP on the figure represents mean values calculated for the survivor animals only at each time point.

Control Experiments

In control rats, ten minutes after the completion of the surgical procedure, glibenclamide (n=4) or tolazamide (n=4) was administered as a 10 mg/kg slow i.v. bolus in 0.3 ml saline, followed by an infusion of 10 mg/kg/h in 0.3 ml. Thereafter, MAP was monitored until t=60 min.

Statistical Analysis

Data are reported as means ± standard error of the mean (SEM). Statistical analysis were performed using analysis of variance (ANOVA). When significant differences were found, Student-Newman-Keuls test was used to identify the differences between specific groups. For comparisons in survival rate, the Chi-square was used. The level of significance was defined as p<0.05.

Results

Figure 1A:
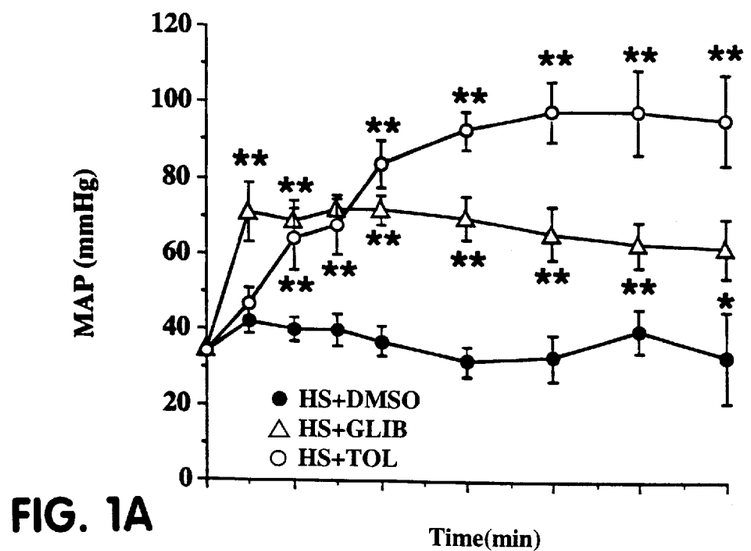
FIGS. 1A and 1B show the effect of glibenclamide and tolazamide treatment on mean arterial pressure (MAP) (FIG. 1A) and survival (FIG. 1B) of anesthetized rats subjected to severe hemorrhagic shock.
Figure 1B:
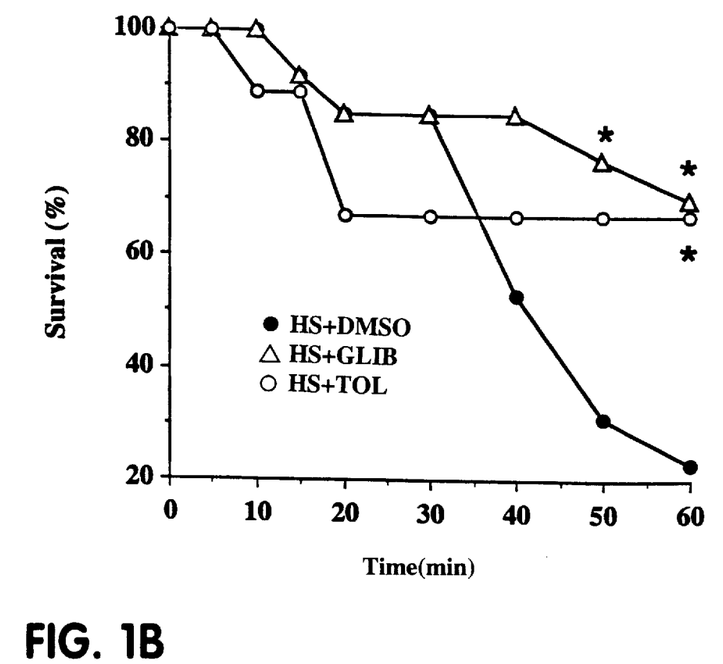

In rats subjected to hemorrhagic shock (HS), MAP remained between 35–45 mm Hg until t=60 min (FIG. 1A). Approximately 80% of the vehicle-treated animals died within 60 min after the hemorrhage (FIG. 1B). Treatment of rats subjected to hemorrhagic shock with glibenclamide or tolazamide raised MAP to approximately 70 mm Hg within 5–10 min. Thereafter, MAP showed a further increase in the tolazamide-treated group, whereas there was a slow decrease in MAP in the glibenclamide-treated group (FIG. 1A). MAP in the groups of rats treated with either $K_{ATP}$ channel blocker remained significantly higher than in the vehicle-treated group. Moreover, at the end of the experiment, at 60 min after the start of the hemorrhage, 3 out of 13 vehicle-treated animals survived, whereas 6 out of 9 and 9 out of 13 animals survived in the groups treated with tolazamide and glibenclamide, respectively. Thus, at t=60 min, both $K_{ATP}$ channel blockers produced a significant (p<0.05) improvement in the rate of survival in rats subjected to hemorrhagic shock (FIG. 1B). There was no significant change in the heart rate at 60 min of HS when compared to controls; heart rate values (control and 60 min value) were 404±15 and 379±22 bpm for the vehicle-treated group, 394±13 and 375±25 bpm for the glibenclamide-treated group, and 368±11 and 356±8 bpm for the tolazamide-treated group.

In the animals treated with glibenclamide or tolazimde, there was no significant difference in the initial pressor responses between the survivor and nonsurvivor animals. For instance, at 15 min, MAP was 70±4 mm Hg in the glibenclamide-treated survivors (n=9) and 73±8 mm Hg in the nonsurvivors (n=4). This suggests that activation of $K_{ATP}$ channels occurs in all animals, but other factors are also involved in determining short-term survival.

In animals anesthetized and instrumented but not subjected to hemorrhagic shock, the same treatment regimen with the $K_{ATP}$ channel blockers did not alter MAP. For instance, MAP in the tolazamide-treated group was 120±5 mm Hg before treatment and 134±5 mm Hg 60 min after the treatment, p>0.05 (n=4), whereas similar values in the glibenclamide-treated group were 122±2 mm Hg before treatment and 115±7 mm Hg 60 min after the treatment, p>0.05 (n=4). These treatments did not cause a significant change in the heart rate (data not shown).

In addition, although glibenclamide, in the dose range used in our study, does not elicit notable hypoglycemia in the rat, hypoglycemia may be one potential side effect in large animal studies or potential human trials. This side effect, however, may be easily overcome with glucose co-administration.

Taken together, these experiments in anesthetized rats demonstrate that inhibition of $K_{ATP}$ channels with glibenclamide or tolazamide markedly improves blood pressure and survival rate in hemorrhagic shock.

Legend to FIGS. 1A and 1B. Effect of glibenclamide and tolazamide treatment on MAP (FIG. 1A) and survival (FIG. 1B) of anesthetized rats subjected to severe hemorrhagic shock. In the control group (HS+DMSO), vehicle (dimethylsulfoxide) for glibenclamide and tolazamide was administered (n=13). In the two treated groups, glibenclamide (HS+GLIB) (n=13) or tolazamide (HS+TOL) (n=9) was administered as a 10 mg/kg slow i.v. bolus in 0.3 ml saline followed by an infusion of 10 mg/kg/h in 0.3 ml saline. Initial MAP values (before the start of the hemorrhage) were 122±5, 114±5, and 119±4 mm Hg in the control group and in the glibenclamide- and tolazamide-treated groups, respectively, and were not significantly different from each other. In FIG. 1A, data represent mean values ±S.E.M. *,**represent significant difference in MAP or survival rate in the two treated groups when compared to vehicle-treated controls (p<0.05 and 0.01 respectively).

Protocol for Examples 2–6

Animal experiments were performed in accordance with NIH guidelines and with the approval of the institutional review board of the Children's Hospital Research Foundation, Cincinnati, Ohio.

Surgical Procedures

Male, immature, random-bred Yorkshire pigs, approximately 6–9 week old and weighing 10–13.5 kg, were deprived of food other than water overnight before surgery. Sedation was achieved with intramuscular ketamine hydrochloride (20 mg/kg) and atropine sulfate (0.05 mg/kg). Endotracheal intubation was performed under 2% isoflurane anesthesia and mechanical ventilation was instituted with a Ventimeter® ventilator (Air Shields, Inc, Hatboro, Pa.). General anesthesia was maintained with 1.5% 10 isoflurane. The respiratory rate and tidal volume were adjusted to maintain the arterial $PCO_2$ at 40±4 torr. In order to eliminate spontaneous ventilation, d-tubocurarine was administered (2 mg/kg iv bolus) as required. Heating pads and blankets were used to maintain the core body temperature at 39.0°±0.4° C.

Swine were instrumented as follows: The right femoral vein was catheterized with a double lumen 5 Fr. catheter for administration of maintenance fluids and drugs (Cook, Bloomington, Ind.). The right femoral artery was catheterized with 5 Fr. single lumen catheter (Cook, Bloomington, Ind.) for measurement of systemic blood pressure and sampling of arterial blood. The left femoral artery was catheterized with a 6 Fr. single lumen catheter (Argon Medical, Athens, Tex.) for blood withdrawal during the shock protocol. A 2.5 Fr. thermistor-tipped catheter (Baxter Healthcare Corporation, Irvine, Calif.) was placed through a cervical cutdown into the right carotid artery and its tip advanced into the ascending aorta. Via a cervical cutdown, a 3 Fr. catheter (Baxter Healthcare Corporation, Irvine, Calif.) was inserted into the right external jugular vein and advanced into the right atrium.

A midline celiotomy was performed, a 16 Fr. Foley catheter inserted into the bladder, and the spleen extirpated in order to prevent the effect of autotransfusion. A 4-mm ultrasonic flow probe was positioned around the renal vein and a 6 mm flow probe placed around the portal vein, for the measurement of renal and portal blood flow (RBF and PBF, respectively)(Transonic Systems, Inc., Ithica, N.Y.). Flow probes were connected to a previously calibrated blood flow meter (Transonic Systems, Inc., Model T206). A 20G 32 mm "Clear-Cath" (Abbot Ireland) catheter was inserted into the portal vein. Two tonometric sigmoid catheters (Tonometrics Inc., Hopkinton, Mass.) were positioned in the lumen of the distal ileum via small antimesenteric enterotomies and secured in place with purse-string sutures. The abdominal cavity was filled with warmed saline and closed in one layer. During the surgical procedure the animals received Ringer's Lactate's solution (RL) at a rate of 20 mL/kg/h. After abdominal closure, the rate of RL infusion was reduced to 10 mL/kg/h and anesthesia was maintained with 0.5% isoflurane, 70% nitrous oxide, and balance oxygen. Swine were allowed to stabilize for at least one hour prior to the onset of hemorrhage.

Hemodynamic Measurements

Mean arterial pressure (MAP), central venous pressure (CVP), and portal venous pressure were determined using calibrated transducers (Cobe Cardiovascular Inc., Arvanda, Col.) driving an amplifier-monitor (Horizon 2000, Mennen Medical Inc., Clarence, N.Y.) with digital readout. Cardiac output (CO) was measured by a computer (Edwards Model 9520A, American Edwards Laboratories, Irvine, Calif.). Room temperature saline (3.0 mL) injectate was rapidly infused via the external jugular vein into the right atrium and the mean of triplicate determinations was recorded. Heart rate (HR) was recorded with a pulse oximeter (Ohmeda 5250 RGM, Louisville, Colo.). Ileal tonometric $PCO_2$ ($TPCO_2$) was measured, as described in Vromen et al., "Protective effects of isopropyl-isothiourea, a potent inhibitor of constitutive nitric oxide synthase in rodent and porcine models of hemorrhagic shock", *Journal of Applied Physiology*, 1996, utilizing 30 min equilibration periods.

Gas tensions in arterial blood, portal blood, and saline obtained from the femoral artery, portal vein, and tonometer, respectively, were measured using a Ciba-Corning 278 blood gas analyzer (Ciba-Corning Diagnostic Corp., Madfield, Mass.). Tonometric estimations of ileal mucosal $PCO_2$ ($TPCO_2$) were performed as described in Salzman et al., "Endotoxin-induced ileal mucosal hyperpermeability in pigs; role of tissue acidosis", *American Journal of Physiology*, 1994, 266:G633–G646. Gas tensions in blood or saline were corrected for core temperature. Oxyhemoglobin and hemoglobin concentrations were measured using a Ciba-Corning 270 CO-Oximeter. Arterial and portal venous lactate were measured by absorption spectrophotometry (Steinberg et al., "Oxygenated cardioplegia: the metabolic functional effects of glucose and insulin", *Ann Thoracic Surg*, 1991, 51:620–629. Blood glucose was measured with Accu-check® Easy™ strips using an Accu-check® Easy™ Glucometer model No. 788 (Boehringer Mannheim Corp., Indianapolis, Ind.).

Cardiac index (CI) was calculated as CO/BW, where BW=Body Weight. Portal blood flow (PBF) and renal blood flow (RBF) were measured directly by transit-time flowmetry. Systemic vascular resistance index (SVRI) was calculated as (MAP-CVP)/CI and mesenteric vascular resistance index (MVRI) defined as (MAP–PVP)/(PBF·BW), where PVP=portal venous pressure. Arterial oxygen content ($CaO_2$) and portal venous oxygen content ($CpO_2$) were calculated using the formulae: $CaO_2=(SaO_2 \cdot 1.36 \cdot [Hb])+(0.0031 \cdot PaO_2)$; $CpO_2=(SpO_2 \cdot 1.36[Hb])+(0.0031, PpO_2)$, whereby $SaO_2$=arterial oxyhemoglobin saturation, $PaO_2$=arterial oxygen tension, $SPO_2$=portal venous oxyhemoglobin saturation, and $PPO_2$=portal venous oxygen tension. Splanchnic oxygen consumption was calculated as $SplVO_2$=(PBF)/BW)·($CaO_2$-$CpO_2$). Splanchnic oxygen extraction was calculated as $SplO_2ext=(CaO_2-CpO_2)/CaO_2$.

Hemorrhagic Shock Protocol

Hemorrhagic Shock (HS) was induced at t=0 min by phlebotomy at a rate of 2 mL/kg/min for 5 min and then at a rate of 1 mL/kg/min, until PBF decreased to 45% of t=0 min. PBF was maintained at this level until t=45 min by additional blood withdrawal as required. No shed blood was retransfused. At t=45 min, animals in Group 2 were resuscitated with RL at a rate of 1 mL/kg/min to match the volume of shed blood. Animals in Group 1 also were treated at t=45 min with the 0.1 mL/kg of the $K_{ATP}$ channel antagonist glibenclamide (in DMSO, administered as an iv bolus over 5 min). Animals in Group 2 received an equivalent volume of the vehicle control (DMSO, 0.1 mL/kg, administered as an iv bolus over 5 min). All pigs survived until t=210 min, with the exception of one animal in Group 2, which died at t=165 min.

Experimental Design

Following a 1 h period of recovery after surgical preparation, the RL infusion was reduced to 6 mL/min. Pigs (n=30) were then randomly assigned in a double-blinded fashion to one of 4 experimental groups. Group 1 (n=10): HS and glibenclamide; Group 2 (n=10): HS and DMSO; Group 3 (n=6): sham-shock and glibenclamide; Group 4 (n=4) sham-shock and DMSO.

Swine were monitored until t=210 min at 5 min intervals during the first hour and at 10 min intervals thereafter for MAP, HR, CVP, RBF, PBF, and portal venous pressure. CO was measured at 15 min intervals during the first hour and every 30 min thereafter. Measurements of arterial and portal venous pH, $PO_2$, $PCO_2$, and hemoglobin and oxyhemoglobin concentrations were obtained every 15 min during the first hour and every 30 min thereafter. Blood glucose levels were measured at the same time intervals, and if the [blood glucose] was below 55 mg/dL, 5% dextrose was added to the RL maintenance infusion. $TPCO_2$ was measured every 30 min. Arterial and portal venous blood samples for lactate determination were obtained at t=0 min, t=45 min, and at 30 min intervals thereafter.

Freeze-clamped biopsies of the ileal mucosa and renal cortex were obtained at t=210 min using steel forceps pre-cooled in liquid nitrogen and stored at −70° C. until further analysis (see Example 6).

Statistical Analysis

Data are reported as means ± standard error of the mean (S.E.M.). Statistical analyses were performed with SPSS software. Comparisons of treated Group versus control groups were evaluated using multivariate analysis of variance (MANOVA), with the pre-treatment measures as covariates. Both Pillais and Hotellings tests were used to assess significant differences between groups. When significant differences were found, univariate F-tests were used to identify the specific Group and time differences. The level of significance was defined as p<0.05.

Results

All pigs survived until T=210 min, with the exception of one shocked animal treated with Ringer's Lactate (RL) alone, which died at T=165 min. Untreated sham-shocked animals had stable hemodynamic, metabolic, and oxygen transport indices for the duration of the study (FIGS. 2–6 and Tables 1 and 2).

EXAMPLE 2

This example (FIGS. 2A–2C) illustrates the effect of glibenclamide on systemic hemodynamics, as shown by the effect of glibenclamide on mean arterial blood pressure (MAP) (FIG. 2A), cardiac index (CI) (FIG. 2B) and systemic vascular resistance index (SVRI) (FIG. 2C) in anesthetized pigs subjected to hemorrhagic shock.

Figure 2A:
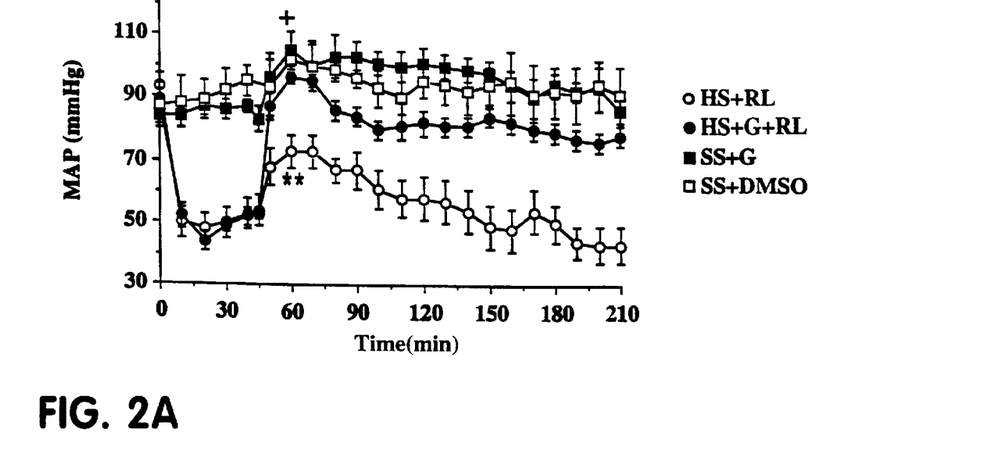
FIGS. 2A–2C show the effect of glibenclamide on mean arterial blood pressure (MAP) (FIG. 2A), cardiac index (CI) (FIG. 2B) and systemic vascular resistance index (SVRI) (FIG. 2C) in anesthetized pigs subjected to hemorrhagic shock.
Figure 2B:
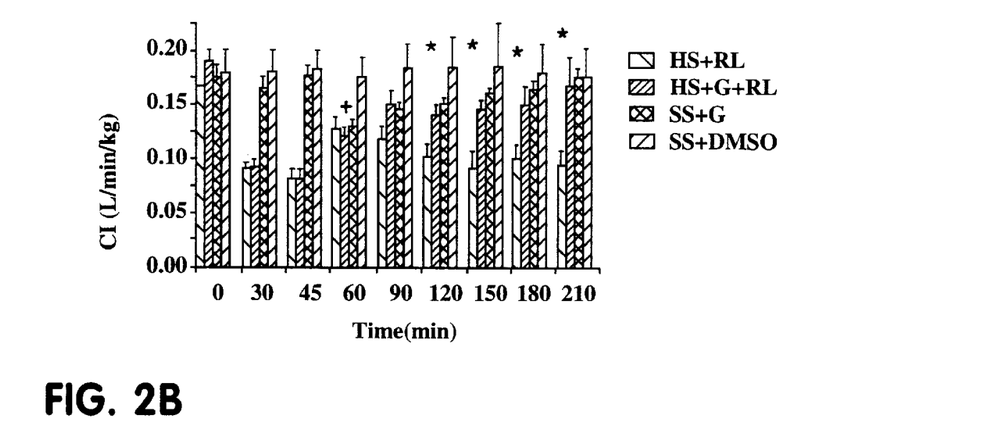

In these experiments, co-administration of glibenclamide with Ringers-Lactate had marked additional benefit in terms of hemodynamic changes. Addition of glibenclamide to the resuscitation fluid produced a sustained restoration of mean arterial pressure (MAP) (FIG. 2A) and cardiac index (CI) (FIG. 2B) to pre-shock levels (FIG. 2A), as opposed to only transient increases produced by RL alone. Treatment of sham-shocked controls with glibenclamide transiently increased MAP and depressed CI, followed by a rapid return to baseline levels (FIGS. 2A–2B).

Figure 2C:
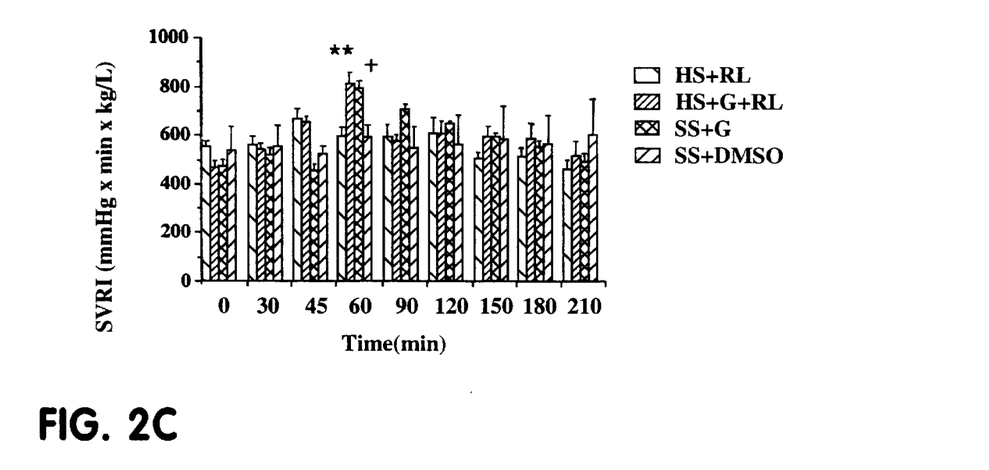

Resuscitation with glibenclamide and RL transiently increased systemic vascular resistance index (SVRI) in shocked animals at t=60 min, followed by a recovery to pre-shock levels by t=90 min (FIG. 2C). In contrast, resuscitation with RL alone had no effect on SVRI. Glibenclamide treatment of sham-shocked controls also caused an immediate but short-lived increase in SVRI (FIG. 2C).

Taken together, these data demonstrate that while Ringers-Lactate only has a transient, and unimpressive beneficial effect on the hemodynamic status in hemorrhagic shock, co-administration of glibenclamide with Ringers-Lactate causes a marked improvement of blood pressure and a sustained improvement in the cardiac output.

The improvement in MAP resulted in part from a pressor action of glibenclamide, as manifested by a transient elevation in SVRI at t=60 min. We also noted that the administration of glibenclamide to sham-shocked control animals resulted in an increase in MAP and SVRI. This latter finding suggests that basal vascular tone in the anesthetized pig is modulated by $K_{ATP}$ channel activity. Given that glibenclamide has pressor effects under basal conditions, but the extent of increase in blood pressure is larger in hemorrhagic shock than in control animals, it is conceivable that the pressor action of the drug in the shocked group results from the combination of two effects: (1) an inhibition of basal vasodilatory tone and (2) a reversal of shock-induced $K_{ATP}$ channel activation.

The glibenclamide-mediated elevation of CI in the shocked pigs persisted and in fact continued to rise after the normalization of SVR. Thus, the data show that $K_{ATP}$ channel inhibitors favorably influence cardiac performance. The basis for the increased cardiac index is presumably an increase in stroke volume, as a result of increased cardiac contractility or improved preload, since there was no evidence of afterload reduction which might secondarily increase CI, nor was there any chronotropic effect. The glibenclamide-mediated increase in stroke volume might represent (1) a venoconstrictive effect, thereby decreasing venous capacitance, augmenting venous return, and improving preload, (2) a direct inotropic effect, or (3) an elevation of diastolic blood pressure, which would be expected to restore coronary perfusion and, thus, cardiac contractility.

Legend to FIGS. 2A–2C. Effect of glibenclamide on mean arterial blood pressure (MAP) (FIG. 2A), cardiac index (CI) (FIG. 2B) and systemic vascular resistance index (SVRI) (FIG. 2C) in anesthetized pigs subjected to HS. 10 mg/kg glibenclamide in DMSO (100 mg/mL) with matched volume of shed blood RL (HS+G+RL) v. 0.1 mL/kg DMSO with matched volume of shed blood RL (HS+RL). SS+G represents sham-shocked pigs that received 10 mg/kg glibenclamide at t=45 min and SS+DMSO represents sham-shocked pigs that received DMSO at t=45 min. Data represent mean values±SEM. $*p<0.05$ and $**p<0.01$ indicate significant differences between treatment paradigms (RL and glibenclamide v.RL alone) in pigs subjected to HS.+ $p<0.05$ indicates differences in sham-shocked pigs receiving glibenclamide at t=60 min v.baseline.

EXAMPLE 3

Figure 3A:
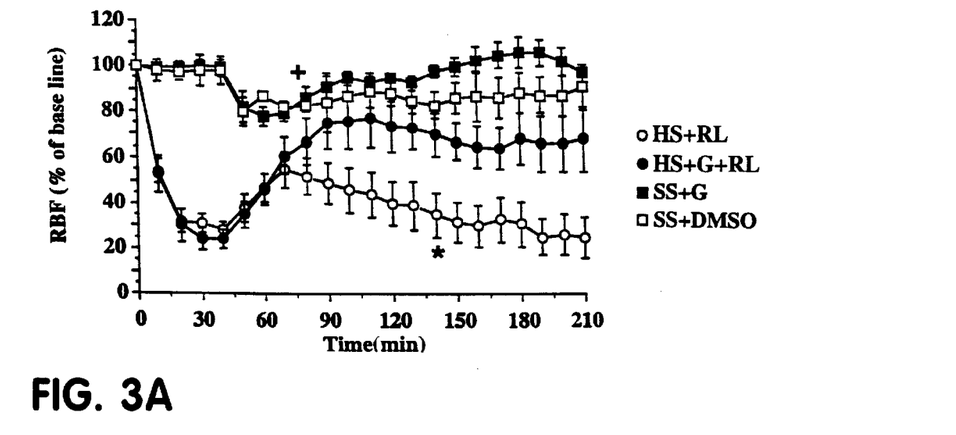
FIGS. 3A–3C show the effect of glibenclamide on renal blood flow (RBF) (FIG. 3A), portal blood flow (PBF) (FIG. 3B) and mesenteric vascular resistance index (MVRI) (FIG. 3C) in anesthetized pigs subjected to hemorrhagic shock.
Figure 3B:
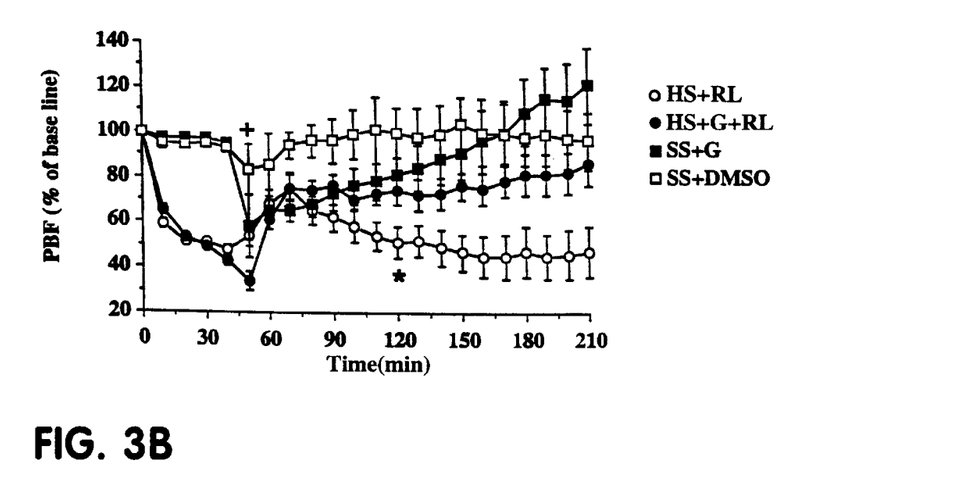
Figure 3C:
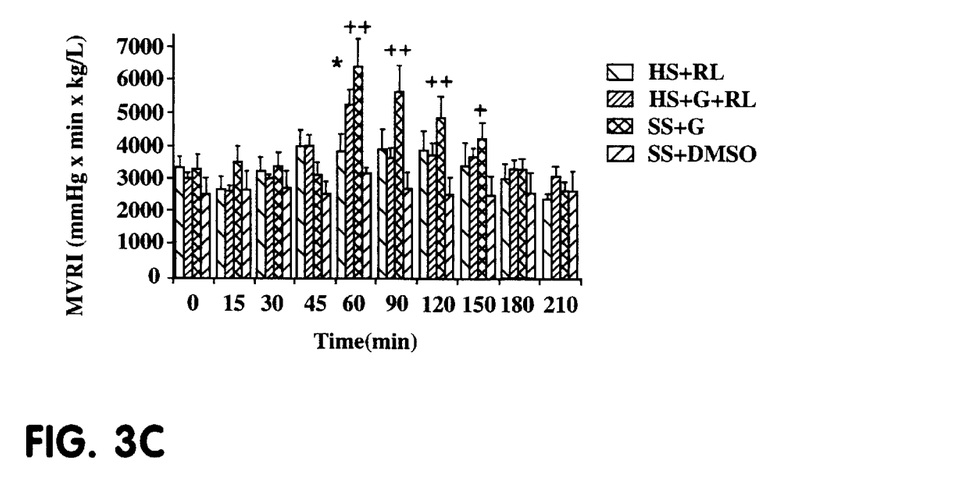

This example (FIGS. 3A–3C) illustrates the effects of glibenclamide on regional hemodynamics in anesthetized pigs subjected to hemorrhagic shock. Addition of glibenclamide to the resuscitation fluid produced a sustained restoration of renal blood flow (RBF) (FIG. 3A) and portal blood flow (PBF) (FIG. 3B) to pre-shock levels, as opposed to only transient increases in RBF and PBF produced by RL alone (FIGS. 3A–B). Resuscitation with glibenclamide and RL caused a large but transient increase in mesenteric vascular resistance index (MVRI) that was not observed following infusion of RL alone (FIG. 3C). Treatment of sham-shocked controls with glibenclamide also caused a major but transient increase in MVRI (FIG. 3C).

Taken together, the data show that the improvement in CI produced by $K_{ATP}$ channel blockade in HS was matched by a concomitant elevation in RBF and PBF. In the absence of glibenclamide, treatment with a low-volume fluid infusion alone provided only a temporary and partial recovery of regional blood flow. MVRI in the pigs receiving glibenclamide was unchanged, except for a brief increase observed directly after the administration of the drug. These data suggest that renal and mesenteric perfusion are not compromised during glibenclamide therapy of hemorrhagic shock.

Legend to FIGS. 3A–3C. Effect of glibenclamide on renal blood flow (RBF) (FIG. 3A), portal blood flow (PBF) (FIG. 3B) and mesenteric vascular resistance index (MVRI) (FIG. 3C) in anesthetized pigs subjected to HS. 10 mg/kg glibenclamide in DMSO (100 mg/mL) with matched volume of shed blood RL (HS+G+RL) v. 0.1 mL/kg DMSO with matched volume of shed blood RL (HS+RL). SS+G represents sham-shocked pigs that received 10 mg/kg glibenclamide at t=45 min and SS+DMSO represents sham-shocked pigs that received DMSO at t=45 min. Data represent mean values ±SEM. $*p<0.05$ indicates significant differences between treatment paradigms (RL and glibenclamide v. RL alone) in pigs subjected to HS.+$p<0.05$ indicates significant differences between sham-shocked pigs receiving glibenclamide v. DMSO (FIGS. 3A and 3B). $++p<0.01,+p<0.05$ indicate significant differences between sham-shocked pigs receiving glibenclamide v. DMSO (FIG. 3C).

EXAMPLE 4

Figure 4A:
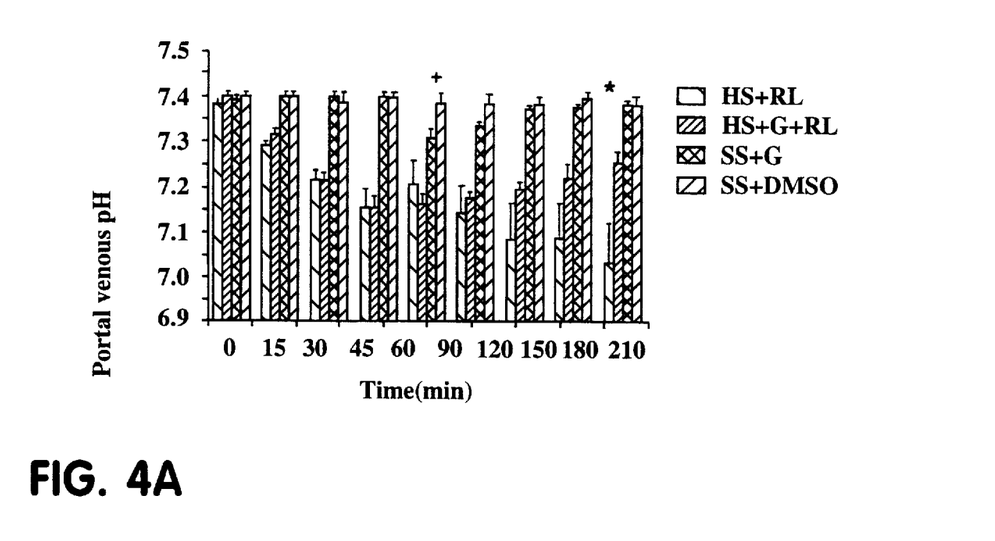
FIGS. 4A and 4B show the effect of glibenclamide on portal venous pH (FIG. 4A) and portal venous oxyhemoglobin concentration (FIG. 4B) in anesthetized pigs subjected to hemorrhagic shock.

This example (FIGS. 4A and 4B) illustrates the effect of glibenclamide on portal venous pH (FIG. 4A) and portal venous oxyhemoglobin concentration (FIG. 4B) in anesthetized pigs subjected to hemorrhagic shock. Portal venous pH partially recovered at t=210 min following resuscitation with RL and glibenclamide (FIG. 4A). In contrast, infusion of shocked animals with RL alone did not prevent a major decline in portal venous pH (FIG. 4A). Glibenclamide had no effect on portal venous pH in sham-shocked animals (FIG. 4A).

Figure 4B:
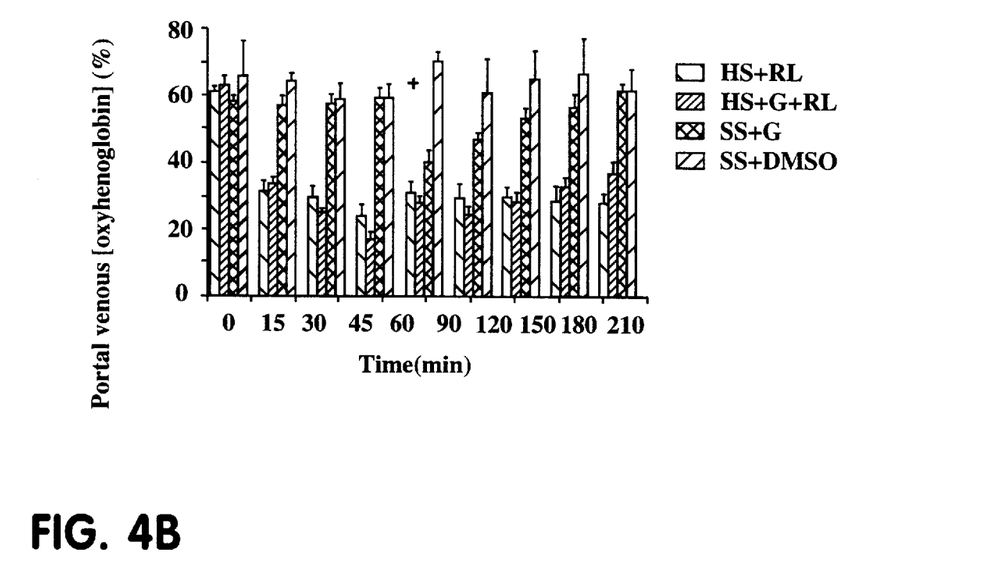

Resuscitation with RL, in the presence or absence of glibenclamide, had no effect on portal venous [oxyHb] (FIG. 4B). In contrast, glibenclamide treatment caused a transient depression of portal [oxyHb] in sham-shocked animals (FIGS. 4 A–B).

Legend to FIGS. 4A–4B. Effect of glibenclamide on portal venous pH(FIG. 4A) and portal venous oxyhemoglobin concentration (FIG. 4B) in anesthetized pigs subjected to HS. 10 mg/kg glibenclamide in DMSO (100 mg/mL) with matched volume of shed blood RL (HS+G+RL) v. 0.1 mL/kg DMSO with matched volume of shed blood RL (HS+RL). SS+G represents sham-shocked pigs that received 10 mg/kg glibenclamide at t=45 min and SS+DMSO represents sham-shocked pigs that received DMSO at t=45 min. Data represent mean values ±SEM. $*p<0.05$ indicates significant differences between treatment paradigms (RL and glibenclamide v. RL alone) in pigs subjected to HS. In FIG. 4A, $+p<0.05$ indicates significant differences between sham-shocked pigs receiving glibenclamide v. DMSO; in FIG. 4B, $+p<0.05$ indicates significant differences between sham-shocked pigs receiving glibenclamide v. DMSO at=90 min v. t=0 min.

EXAMPLE 5

Figure 5A:
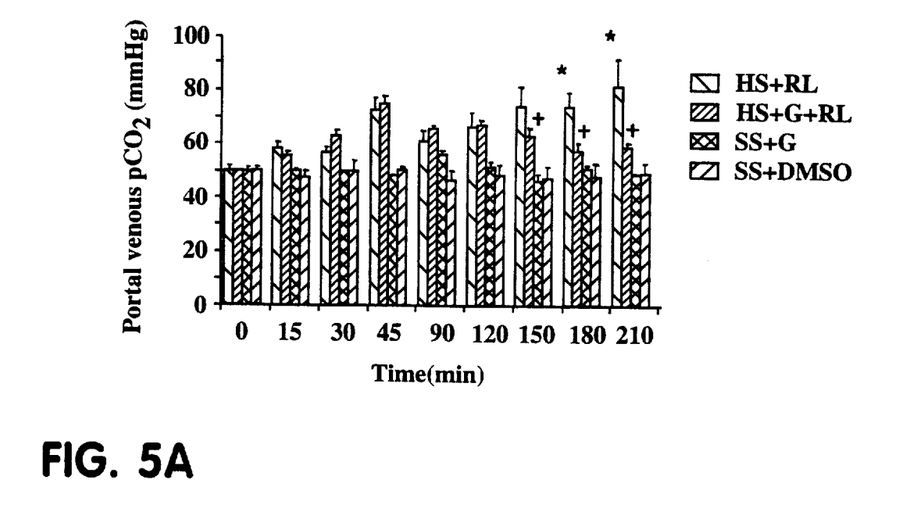
FIGS. 5A and 5B show the effect of glibenclamide on portal venous $PCO_2$ (FIG. 5A) and ileal mucosal tonometric $PCO_2$ (FIG. 5B) in anesthetized pigs subjected to hemorrhagic shock.
Figure 5B:
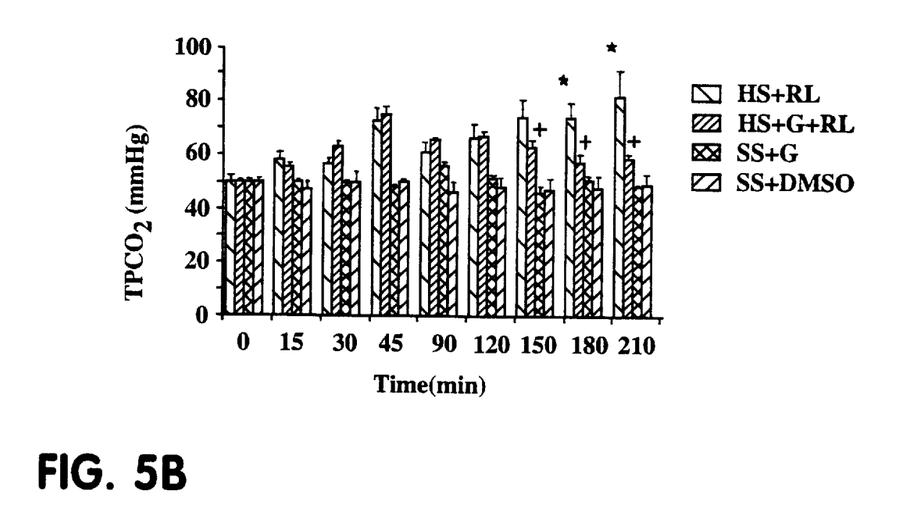

This example (FIGS. 5A–5B) illustrates the effect of glibenclamide on portal venous $PCO_2$ and ileal tonometric $PCO_2$ ($TPCO_2$) in anesthetized pigs subjected to hemorrhagic shock. Addition of glibenclamide to the resuscitation fluid caused a sustained reduction in portal venous $PCO_2$ and $TPCO_2$ to pre-shock levels (FIGS. 5A–B). In contrast, infusion of RL alone to shocked animals resulted in a significant increase in portal venous $PCO_2$ and $TPCO_2$ (FIGS. 5A–B). Glibenclamide infusion had no effect on portal venous $PCO_2$ and $TPCO_2$ in sham-shocked animals (FIGS. 5A–B).

Legend to FIGS. 5A–5B. Effect of glibenclamide on portal venous $PCO_2$ (FIG. 5A) and $TPCO_2$ (FIG. 5B) in anesthetized pigs subjected to HS. 10 mg/kg glibenclamide in DMSO (100 mg/mL) with matched volume of shed blood RL (HS+G+RL) v. 0.1 mL/kg DMSO with matched volume of shed blood RL (HS+RL). SS+G represents sham-shocked pigs that received 10 mg/kg glibenclamide at t=45 min and SS+DMSO represents sham-shocked pigs that received DMSO at=45 min. Data represent mean values ±SEM. *p<0.05 indicates significant differences between treatment paradigms (RL and glibenclamide v. RL alone) in pigs subjected to HS; +p<0.05 indicates significant differences between sham-shocked pigs receiving glibenclamide v. DMSO.

EXAMPLE 6

This example (FIGS. 6A and 6B, and Tables 1 and 2) illustrates the effect of glibenclamide on oxygen transport and tissue metabolism in anesthetized pigs subjected to hemorrhagic shock. For the determination of tissue high energy phosphates, tissue samples (obtained as described in "Experimental Design" section, above) were homogenized in 1 mL of cold 0.6M perchloric acid in a glass tube immersed in an ice bath. The samples were neutralized with 0.9 mL of a 1.0M potassium phosphate buffer (pH=12), centrifuged for 10 min (1,500 g) in order to remove precipitated proteins, and filtered through a 0.2 m Gelman Acrodisc syringe filter. Supernatants were assayed for ATP and ATP metabolites (as described by Munfakh et al., "Protection of the hypertrophied myocardium by crystalloid cardioplegia", *Journal of Surgical Research,* 1991, 51:447–456) using a Beckman model 231 HPLC instrument equipped with a Waters Wisp auto injector. For determinations of ATP, ADP, and AMP, aliquots of the samples were analyzed on a Whatman SAX-10 ion exchange column, utilizing a mobile phase consisting of 0.16 m $KH_2PO_4$ and 0.1M KCI in deionized water (pH=6.5) at a flow rate of 1.5 mL/min. ATP metabolites were detected by UV absorption spectrophotometry and quantitated using external standards. The protein content of samples was assayed by the Lowry method (Lowry et al., "Protein measurement with the folin phenol reagent", *J Biochem,* 1951, 193:265–275).

The addition of glibenclamide to the resuscitation fluid had no effect on portal venous oxygen content and splanchnic oxygen extraction (Table 1). Treatment of sham-shocked animals with glibenclamide transiently decreased portal venous oxygen content and increased splanchnic oxygen extraction. Splanchnic oxygen consumption was equivalent in all four groups.

Addition of glibenclamide to the resuscitation fluid caused a delayed recovery of arterial and portal venous [lactate], whereas treatment of shocked animals with RL alone resulted in a steady increase in arterial and portal venous [lactate] (Table 2).

Figure 6A:
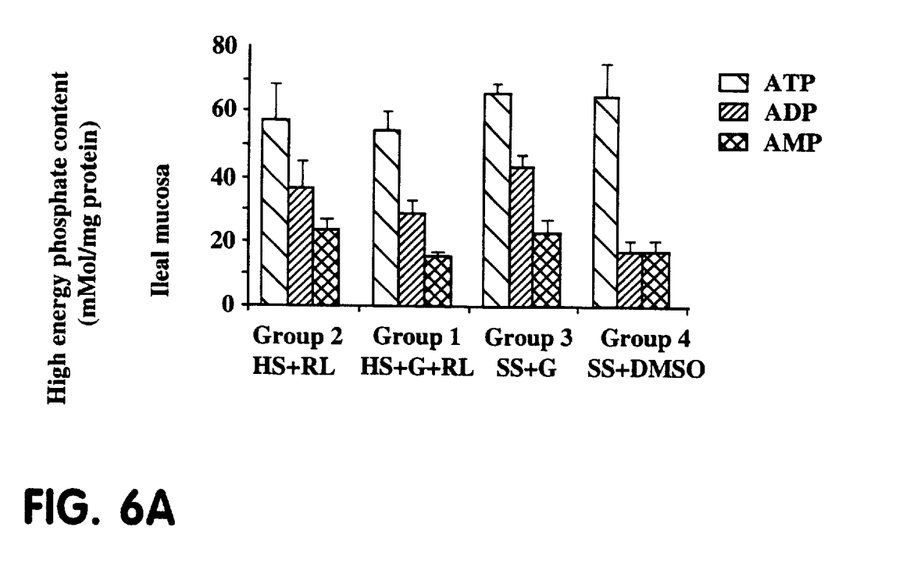
FIGS. 6A and 6B show the effect of glibenclamide treatment on ATP, ADP and AMP content of ileal mucosa (FIG. 6A) and kidney (FIG. 6B), in pigs subjected to hemorrhagic shock.
Figure 6B:
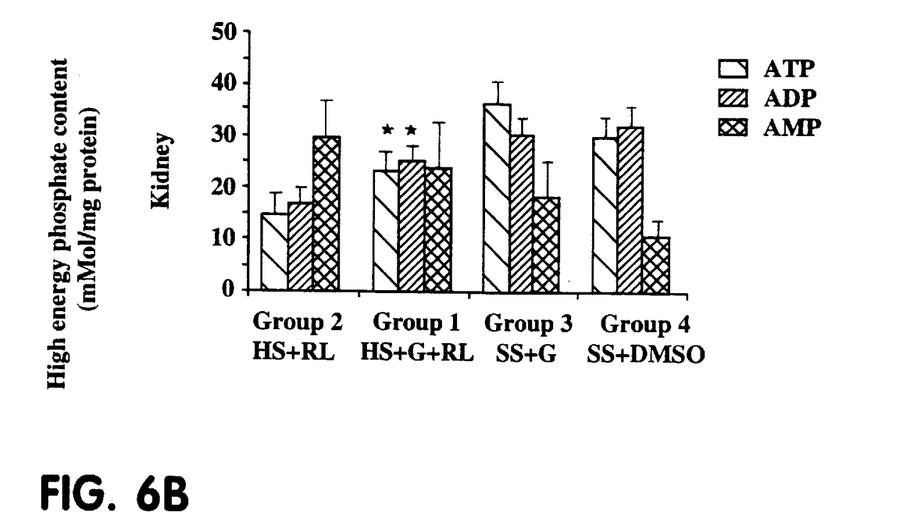

Hemorrhagic shock caused a decrease in ATP and ADP content in the kidney but not in the ileal mucosa (FIGS. 6A and 6B). Treatment with glibenclamide had no effect on ileal mucosal [ATP], [ADP], [AMP], and energy charge (FIG. 6A), but improved renal cortical [ATP] and [ADP] (FIG. 6B) (p<0.05).

Taken together, the data presented in Examples 5 and 6 show that treatment with Ringers-Lactate and glibenclamide caused more pronounced therapeutic benefit than Ringers-Lactate alone in terms of renal cortical [ATP], ileal mucosal $pCO_2$, and serum lactate.

Legend to FIG. 6. Effect of glibenclamide treatment on ATP, ADP and AMP content of ileal mucosa and kidney, in pigs subjected to hemorrhagic shock. Samples were taken at 210 min after the initiation of shock. Data represent mean values ±SEM. Values are represented in nMol/mg protein. There was a significant decrease in ATP and ADP content in hemorrhagic shock in the kidney but not in the ileal mucosa (p<0.05). *p<0.05 indicates significant difference between Group 2 and Group 1.

TABLE 1

Effect of glibenclamide treatment on portal oxygen content ($CpO_2$; mL/dL), splanchnic oxygen consumption ($SpIVO_2$, mL/min/kg) and splanchnic oxygen extraction ($SpIO_2$, %) in pigs subjected to hemorrhagic shock.

|  |  | Baseline | 45 min | 90 min | 120 min | 150 min | 210 min |
|---|---|---|---|---|---|---|---|
| $CpO_2$ | Group 1 | 7.18 ± 0.39 | 1.91 ± 0.25** | 2.41 ± 0.21 | 2.13 ± 0.21** | 2.47 ± .28** | 3.10 ± 0.24** |
|  | Group 2 | 7.94 ± 0.56 | 2.75 ± 0.38** | 3.32 ± 0.48*4 | 3.06 ± 0.50** | 2.96 ± 0.50** | 2.71 ± 0.50** |
|  | Group 3 | 7.15 ± 0.38 | 7.20 ± 0.54 | 4.86 ± 0.48&* | 5.25 ± 0.24&* | 6.76 ± 0.40 | 7.52 ± 0.42 |
|  | Group 4 | 8.56 ± 0.97 | 7.43 ± 0.69 | 9.22 ± 0.87 | 7.35 ± 0.50 | 8.27 ± 0.90 | 8.23 ± 0.80 |
| $SpIVO_2$ | Group 1 | 142 ± 9.4 | 107.2 ± 12.2 | 131.9 ± 10.6 | 145.1 ± 17.9 | 137.3 ± 14 | 127.7 ± 16.5 |
|  | Group 2 | 152.1 ± 20.5 | 119.6 ± 18.8 | 121.3 ± 16.7 | 106.0 ± 19.0 | 98.3 ± 20.8 | 129.1 ± 17.2 |
|  | Group 3 | 142.7 ± 22.4 | 141.6 ± 21.1 | 140.4 ± 27.4 | 147.0 ± 30.5 | 135.4 ± 25.0 | 156.2 ± 30.8 |
|  | Group 4 | 128.3 ± 36.2 | 186.5 ± 18.8 | 134.7 ± 21.7 | 190.1 ± 13.7 | 191.5 ± 22.0 | 157.3 ± 20.5 |
| $SPLO_2$ | Group 1 | 41.4 ± 3.5 | 82.3 ± 2.1** | 78.2 ± 1.844 | 75.6 ± 3.0** | 71.1 ± 3.5** | 65.0 ± 3.3** |
|  | Group 2 | 40.7 ± 2.7 | 76.1 ± 2.8** | 72.1 ± 3.644 | 70.7 ± 4.8** | 71.4 ± 4.4** | 76.5 ± 4.5** |
|  | Group 3 | 43.8 ± 9.0 | 41.8 ± 4.3 | 62.1 ± 3.6&& | 57.9 ± 2.1&& | 45.7 ± 3.5 | 40.8 ± 3.5 |
|  | Group 4 | 30.4 ± 9.5 | 41.8 ± 6.4 | 39.5 ± 1.9 | 44.0 ± 6.0 | 36.7 ± 7.6 | 39.0 ± 7.2 |

Data represent mean values ± SEM. **(p < 0.01), *(p < 0.05) significantly different from baseline. &&(p < 0.01), &(p < 0.05) significantly different from Group 4.

TABLE 2

Effect of glibenclamide on arterial and portal blood lactate fevel, in pigs subjected to hemorrhagic shock.

|  |  | Baseline | 45 min | 90 min | 120 min | 150 min | 180 min | 210 min |
|---|---|---|---|---|---|---|---|---|
| Arterial | Group 1 | 0.8 ± 0.1 | 2.8 ± 0.3** | 5.4 ± 0.6** | 5.1 ± 0.8** | 4.3 ± 0.6** | 3.6 ± 0.6** | 3.5 ± 0.8** |
|  | Group 2 | 0.8 ± 0.1 | 2.6 ± 0.3** | 3.2 ± 0.7** | 3.3 ± .07 | 5.7 ± 1.7** | 5.1 ± 1.6** | 0.6 ± 0.1 |
|  | Group 3 | 0.9 ± 0.2 | 1.0 ± 0.2 | 1.3 ± 0.2 | 0.9 ± 0.1 | 0.8 ± 0.1 | 0.7 ± 0.2 | 0.6 ± 0.1 |
|  | Group 4 | 1.3 ± 0.2 | 0.8 ± 0.1 | 0.9 ± 0.2 | 0.7 ± 1.0 | 0.7 ± 0.2 | 0.6 ± .2 | 0.7 ± 0.2 |
| Portal | Group 1 | 1.1 ± 0.1 | 4.0 ± 0.5** | 6.0 ± 1.0** | 6.9 ± 1.5** | 4.5 ± 0.8** | 3.7 ± 0.7** | 3.3 ± 0.7** |
|  | Group 2 | 1.0 ± 0.1 | 3.3 ± 0.5** | 3.5 ± 0.9** | 4.9 ± 1.3** | 6.8 ± 1.9** | 5.9 ± 1.8** | 6.0 ± 1.4** |
|  | Group 3 | 1.0 ± 0.2 | 0.9 ± 0.2 | 1.0 ± 0.2 | 0.8 ± 0.1 | 0.9 ± 0.1 | 0.7 ± 0.1 | 0.7 ± 0.1 |
|  | Group 4 | 1.4 ± 0.1 | 0.9 ± 0.2 | 1.0 ± 0.3 | 0.8 ± 0.2 | 0.9 ± 0.1 | 1.0 ± 0.4 | 0.7 ± 0.1 |

Values are represented in mMol/L.
**significantly different from baseline ($p < 0.01$)

What is claimed is:

1. A method for inhibiting or treating hemorrhagic shock in a mammal, comprising the step of:

administering to said mammal an amount of a $K_{ATP}$ channel inhibitor sufficient to inhibit or treat hemorrhagic shock in said mammal wherein said $K_{ATP}$ channel inhibitor is a sulfonylurea.

2. The method of claim 1 wherein said sulfonylurea is selected from the group consisting of glibenclamide, tolazamide, acetohexamide, tolbutamide and combinations thereof.

3. The method of claim 1 wherein said sulfonylurea is selected from the group consisting of glibenclamide, tolazamide, and combinations thereof.

4. The method of claim 1 wherein said $K_{ATP}$ channel inhibitor is administered parenterally.

5. The method of claim 4 wherein said $K_{ATP}$ channel inhibitor is administered in a pharmacologically acceptable carrier, said carrier being selected from the group consisting of Ringers-Lactate, a sodium chloride solution, red blood cells, whole blood, plasma, a crystalloid solution, a colloid solution, dextrose, albumin, ethanol, sodium hydroxide, dimethylsulfoxide, water and combinations thereof.

6. The method of claim 4 wherein said $K_{ATP}$ channel inhibitor is administered in a pharmacologically acceptable carrier thereby forming a composition, said carrier comprising Ringers-Lactate with 10% (wt/vol) dextrose.

7. The method of claim 6 wherein said $K_{ATP}$ channel inhibitor represents from about 0.01% (wt/vol) to about 10% (wt/vol) of said composition.

8. The method of claim 4 wherein said $K_{ATP}$ channel inhibitor is administered in combination with another ingredient selected from the group consisting of an anti-oxidant, a sedative, an anesthetic, a catecholamine, an antibiotic, a glucocorticoid, a histamine receptor blocker, calcium, a bacteriostat, an inhibitor of a free-radical-producing enzyme, a non-steroidal anti-inflammatory agent, a suspending agent, a stabilizing agent, a color, a dye, a preservative and combinations thereof.

9. The method of claim 1 wherein said $K_{ATP}$ channel inhibitor is administered at a dose of from about 5 mg/day to about 17.5 g/day.

10. The method of claim 1 wherein said $K_{ATP}$ channel inhibitor is administered at a dose of from about 5 mg/day to about 10 g/day.

11. The method of claim 1 wherein said $K_{ATP}$ channel inhibitor is administered at a dose of from about 200 mg/day to about 5 g/day.

12. The method of claim 1 wherein said $K_{ATP}$ channel inhibitor is administered in an amount sufficient to improve a parameter adversely affected by blood loss, said parameter selected from the group consisting of systemic hemodynamics, regional hemodynamics, tissue metabolism and combinations thereof.

13. The method of claim 1 further comprising the step of administering a resuscitation fluid to said mammal.

14. The method of claim 13 wherein said resuscitation fluid is selected from the group consisting of Ringers-Lactate, a sodium chloride solution, red blood cells, whole blood, plasma, a crystalloid solution, a colloid solution, dextrose, albumin, ethanol, sodium hydroxide, dimethylsulfoxide, water and combinations thereof.

* * * * *